United States Patent
Inokuchi et al.

(10) Patent No.: US 8,234,130 B2
(45) Date of Patent: Jul. 31, 2012

(54) METHOD FOR CREATING MEDICAL TREATMENT MODELS FROM A DATABASE OF MEDICAL RECORDS

(75) Inventors: Akihiro Inokuchi, Suita (JP); Naohiko Uramoto, Yokohama (JP)

(73) Assignee: International Business Machines Corporation, Armonk, NY (US)

( * ) Notice: Subject to any disclaimer, the term of this patent is extended or adjusted under 35 U.S.C. 154(b) by 599 days.

(21) Appl. No.: 11/915,851

(22) PCT Filed: Jun. 8, 2006

(86) PCT No.: PCT/JP2006/311533
§ 371 (c)(1),
(2), (4) Date: Jan. 10, 2010

(87) PCT Pub. No.: WO2006/132320
PCT Pub. Date: Dec. 14, 2006

(65) Prior Publication Data
US 2010/0105989 A1    Apr. 29, 2010

(30) Foreign Application Priority Data
Jun. 8, 2005 (JP) .................... 2005-168921

(51) Int. Cl.
*G06Q 50/00* (2006.01)
(52) U.S. Cl. .................... 705/3; 705/2; 600/300
(58) Field of Classification Search .......... 705/2–3; 600/300
See application file for complete search history.

(56) References Cited

U.S. PATENT DOCUMENTS

| | | | |
|---|---|---|---|
| 2001/0037056 A1 | 11/2001 | Nunome | 600/300 |
| 2004/0078241 A1* | 4/2004 | Shiobara | 705/3 |
| 2004/0103001 A1 | 5/2004 | Mazar et al. | 705/2 |
| 2004/0122714 A1* | 6/2004 | Kuth et al. | 705/2 |

FOREIGN PATENT DOCUMENTS

| | | |
|---|---|---|
| EP | 1 169 964 A2 | 1/2002 |
| JP | 2004-185547 | 7/2004 |
| WO | WO 2006/132320 A1 | 12/2006 |

OTHER PUBLICATIONS

Marianne Mchee, Mayo Builds Toward Customized Medicine, Aug. 9, 2004, Information Week, p. 24.*

Motoyama et al., Knowledge Discovery from Inconstant Time Series Data, SIG-KBS-A405-05 (2/25), pp. 27-32.

Lin et al., Mining Time Dependency Patterns in Clinical Pathways, International Journal of Medical Informatics, vol. 62, Issue 1, pp. 11-25 (2001).

* cited by examiner

*Primary Examiner* — Gerald J. O'Connor
*Assistant Examiner* — Sind Phongsvirajati
(74) *Attorney, Agent, or Firm* — Ido Tuchman; William J. Stock

(57) ABSTRACT

A medical guide service for a doctor, a patient, a general user, and a medical institution. The medical guide system may include a unit that creates medical record data and a unit that extracts the medical record data for each patient. The unit that extracts the medical record data uses examination data before a predetermined dividing point in a chronological order as before-dividing-point data and treatment data after the predetermined dividing point in the chronological order as after-dividing-point data. A unit extracts a treatment pattern from the after-dividing-point data. Another unit derives a rule that associates the examination results with the treatment pattern from the treatment pattern and the before-dividing-point data.

16 Claims, 8 Drawing Sheets

FIG. 1

| PATIENT ID | EXAMINATION DATA 1 (DATE AND TIME OF EXAMINATION EXAMINATION ITEM EXAMINATION RESULT) | | | ... | TREATMENT DATA 1 (DATE AND TIME OF TREATMENT TREATMENT BEHAVIOR OUTCOME) | | | ... | OTHERS |
|---|---|---|---|---|---|---|---|---|---|
| 01234567 | 2004/1/13 | xxxxx | 2.1 | ... | 2004/1/20 | OPERATIVE METHOD 1 | COMPLETE RECOVERY | ... | ... |

FIG. 2

■PHYSICAL EXAMINATION
  - BLOOD TEST
    ・ABO
    ・LEUKOCYTE
      - NUMBER OF LEUKOCYTES
    ・ANEMIA
      - NUMBER OF ERYTHROCYTES
      - MEAN CORPUSCULAR HEMOGLOBIN
      - Ht
      - MCV
      - MCH
      - MCHC
    ・BLOOD PLATELET
      - NUMBER OF BLOOD PLATELETS
    ・LIVER FUNCTION
      - GOT
      - GPT
      - γGTP
    ・SEBACEOUS CONSTITUTION
      - TOTAL AMOUNT OF CHOLESTEROL
      - NEUTRAL FAT
      - HDL
      - LDL
  - URINE EXAMINATION
    ・GLYCOMETABOLISM
    ・URIC ACID
      - AMOUNT OF GLUCOSE IN URINE
      - BLOOD SUGAR LEVEL ON EMPTY STOMACH
    ・RENAL FUNCTION
      - CREATININE
      - AMOUNT OF PROTEIN IN URINE
    ・...
  - ...
■HISTODIAGNOSIS
  - ...
■CYTOLOGIC DIAGNOSIS
  - ...

CLASSIFICATION SYSTEM OF EXAMINATION ITEMS

■OPERATION
  - SURGICAL OPERATION
    ・TOTAL EXTIRPATION
    - ...
    ・PARTIAL EXCISION
  - OPERATIVE METHOD 1
  - OPERATIVE METHOD 2
  - ...
■RADIATION TREATMENT
  - RADIATION TREATMENT 1
  - RADIATION TREATMENT 2
  - ...
■CHEMOTHERAPY
  - CHEMOTHERAPY 1
  - CHEMOTHERAPY 2
  - ...
■CLINICAL TRIAL
  - CLINICAL TRIAL 1
  - CLINICAL TRIAL 2
■PRESCRIPTION
  - ...

CLASSIFICATION SYSTEM OF TREATMENT BEHAVIORS

CHRONOLOGICAL ORDER OF EXAMINATIONS AND
TREATMENTS RELATED TO PATIENT HAVING ID 01234567

FIG. 4

| PATIENT ID | DATE | TREATMENT BEHAVIOR, EXAMINATION ITEM |
|---|---|---|
| 01234567 | 2004/1/20 | OPERATIVE METHOD 1, X-RAY INSPECTION |
| 01234567 | 2004/1/22 | RADIATION TREATMENT |
| 01234567 | 2004/1/23 | X-RAY INSPECTION |
| ⋮ | ⋮ | ⋮ |

TABLE B

CONVERSION INTO TRANSACTION DATA

PATENT ID 1 = : { OPERATIVE METHOD 1, X-RAY INSPECTION, RADIATION TREATMENT, X-RAY INSPECTION, PRESCRIPTION 1, PRESCRIPTION 2, PRESCRIPTION 19, COMPLETE RECOVERY }
PATIENT ID 2 = : { CLINICAL TRIAL, CHEMOTHERAPY 4, DEATH }

PATENT ID n = : { ⋯ }

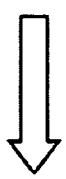

EXTRACT COMBINATION OF TREATMENT BEHAVIORS THAT ARE LARGER THAN MINIMUM NUMBER OF RECORDS (THRESHOLD VALUE)

| PATIENT ID | COMBINATION 1 (SURGICAL OPERATION, NO MEDICAL TREATMENT) | ... | COMBINATION m (SURGICAL OPERATION, COMPLETE RECOVERY ···) |
|---|---|---|---|
| 1 | ○ | ... | × |
| ⋮ | ⋮ | ⋮ | ⋮ |
| n | × | ... | ○ |

TABLE C

○ INDICATES THAT RECORD INCLUDES COMBINATION

FIG. 5

| PATIENT ID | COMBINATION 1 (SURGICAL OPERATION, NO MEDICAL TREATMENT) | ... | COMBINATION m (SURGICAL OPERATION, COMPLETE RECOVERY ···) |
|---|---|---|---|
| 1 | ○ | ... | × |
| ⋮ | ⋮ | ⋮ | ⋮ |
| n | × | ... | ○ |

TABLE C

| | TABLE A | | | | PATTERN |
|---|---|---|---|---|---|
| PATIENT ID | EXAMINATION xxxxx | EXAMINATION yyyyy | ... | EXAMINATION zzzzz | COMBINATION 1 (SURGICAL OPERATION, NO MEDICAL TREATMENT) |
| 1 | 2.1 | 4.6 | ... | 7.2 | ○ |
| ⋮ | ⋮ | ⋮ | ⋮ | ⋮ | ⋮ |
| n | 7.2 | 6.4 | ... | 9.4 | × |

TABLE D

FIG. 6

| CATEGORY | EXAMINATION | TREATMENT | OUTCOME | NUMBER OF RECORDS |
|---|---|---|---|---|
| ☐ CATE<br>♦☐ STAGE<br>♦☐ OUTCOME<br>♦☐ NAME OF DISEASE<br>☐ CLASSIFICATION<br>♦☐ 1<br>♦☐ 2 | C-Cr 2 TIME METHOD · BLOOD SERUM <=0.7 AND MONO >= 0.2 OR NCC<10.45 AND PREVIOUS ACTH >= 13.6 AND SPECIFIC GRAVITY < 1.007 OR AMOUNT OF PROTEIN IN URINE >= 10 AND CD79a >= 95.4 | SURGICAL OPERATION (087654321), SURGICAL OPERATION | REMISSION | 18 |
| ♦☐ SAMPLE<br>📄 BACTERIA<br>♦☐ PATHOLOGY<br>♦☐ PHYSIOLOGY<br>♦☐ ENDOSCOPE<br>♦☐ RADIATION<br>♦☐ RI<br>📄 PRESCRIPTION<br>♦☐ INJECTION<br>📄 REHABILITATION<br>📄 TREATMENT<br>♦☐ SURGICAL OPE<br>📄 SURGICAL OPE<br>♦☐ BLOOD TRANSFUSION<br>📄 RADIATION TREATMENT<br>📄 NUTRITION<br>📄 INSTRUCTION OF NURSING<br>📄 CLINICAL TRIAL<br>📄 RESERVATION OF EXAMINATION<br>📄 OTHER HOSPITAL<br>📄 DOCUMENT<br>♦☐ 3<br>♦☐ 4<br>♦☐ B<br>♦☐ P<br>♦☐ S | 180 PROTACTIN >= 14.5 OR PgR = (+) AND CARBAMAZEPINE <= 5.2 AND URINE AMY-P1 >= 41.5 | TOTAL EXTIRPATION, SURGICAL OPERATION | | 147 |
| | INCLUSION = 0-1/ PER AND URATE = 2+ AND U-H-D >= 0.44 OR CD8 >=34.9 OR 120 CORTISOL >= 11.8 AND M-B · S >= 0.0 AND ml/min >= 128.9 | SURGICAL OPERATION, RADIATION TREATMENT 4, RADIATION TREATMENT | TREATMENT | 34 |
| | UROBILINOGEN = n AND URINE AMY-P1 <=41.5 AND CD7 >= 0.2 OR RUBELLA IgG ANTIBODY = (+) OR SPECIFIC GRAVITY >= 1.004 AND URINE AMY-P1 <= 41.5 | SURGICAL OPERATION (012345679), SURGICAL OPERATION, CHEMOTHERAPY 4, CHEMOTHERAPY | | 10 |
| | CD20 >= 22.7 AND WAXY CAST = 0-1/ PER | | COMPLETE RECOVERY | 13 |
| | ERYTHROBLAST >= 0 AND U-K-D >= 148 AND KETONE BODY 4 = - OR N-BAND >= 11.7 AND ADRENALINE <= 28 AND ANTIBODY AB = ANTIBODY B OR ZONISAMIDE < 10.5 | CHEMOTHERAPY, RADIATION TREATMENT 3, RADIATION TREATMENT | REMISSION | 11 |
| | EBIgG ANTIBODY = (+) OR ml/min = 128.9 | CLINICAL TRIAL 2 | | 102 |
| | E-MYEL >=0.0 AND HLA-ABC < 100.0 OR SINDAN 11 = KYUKEIHA AND 60 PROLACTIN <18.8 AND PLASMINOGEN = 131 | RADIATION TREATMENT | COMPLETE RECOVERY | 22 |
| KIND  C34%<br>NUMBER OF RECORDS  6<br>DIVIDING POINT  2 | MCHC > 35.8 AND TOTAL AMOUNT OF PROTEIN > 7 AND SPECIFIC GRAVITY <= 1,014 AND T-CO2 >27.6 AND CONCENTRATION OF HEMOGLOBIN <= 9.5 OR MCHC > 35.8 AND TOTAL AMOUNT OF PROTEIN IN URINE > 7 AND SPECIFIC GRAVITY <= 1,014 AND URIC ACID > 8.2 OR | SURGICAL OPERATION | REMISSION | 6 |
| EXECUTE | MINIMUM NUMBER OF RECORDS: 6 | | | |
| MINING | | | | |

FIG. 7

| EXAMINATION | TREATMENT | OUTCOME | NUMBER OF PERSONS |
|---|---|---|---|
| STAGE>1 AND STAGE 3 ← ... | SURGICAL OPERATION (087654321), SURGICAL OPERATION, ... | REMISSION | 18 |

| PATIENT ID | NAME | DATE OF BIRTH | DATE OF FIRST EXAMINATION |
|---|---|---|---|
| 01234567 | ABCD EFG | 1988.11.22 | 2004.10.01 AM 9:15 |
| ⋮ | ⋮ | ⋮ | ⋮ |

FIG. 8

```
CREATE ELECTRONIC MEDICAL RECORD DATA — 810
           ↓
CREATE TABLES A AND B BEFORE AND AFTER DIVIDING POINT — 820
           ↓
CONVERT TABLE INTO TRANSACTION DATA — 830
           ↓
EXTRACT FREQUENT GENERALIZED PATTERN (TABLE C) — 840
           ↓
ADD FREQUENT GENERALIZED PATTERN TO TABLE A (TABLE D) — 850
           ↓
MAKE RULE — 860
```

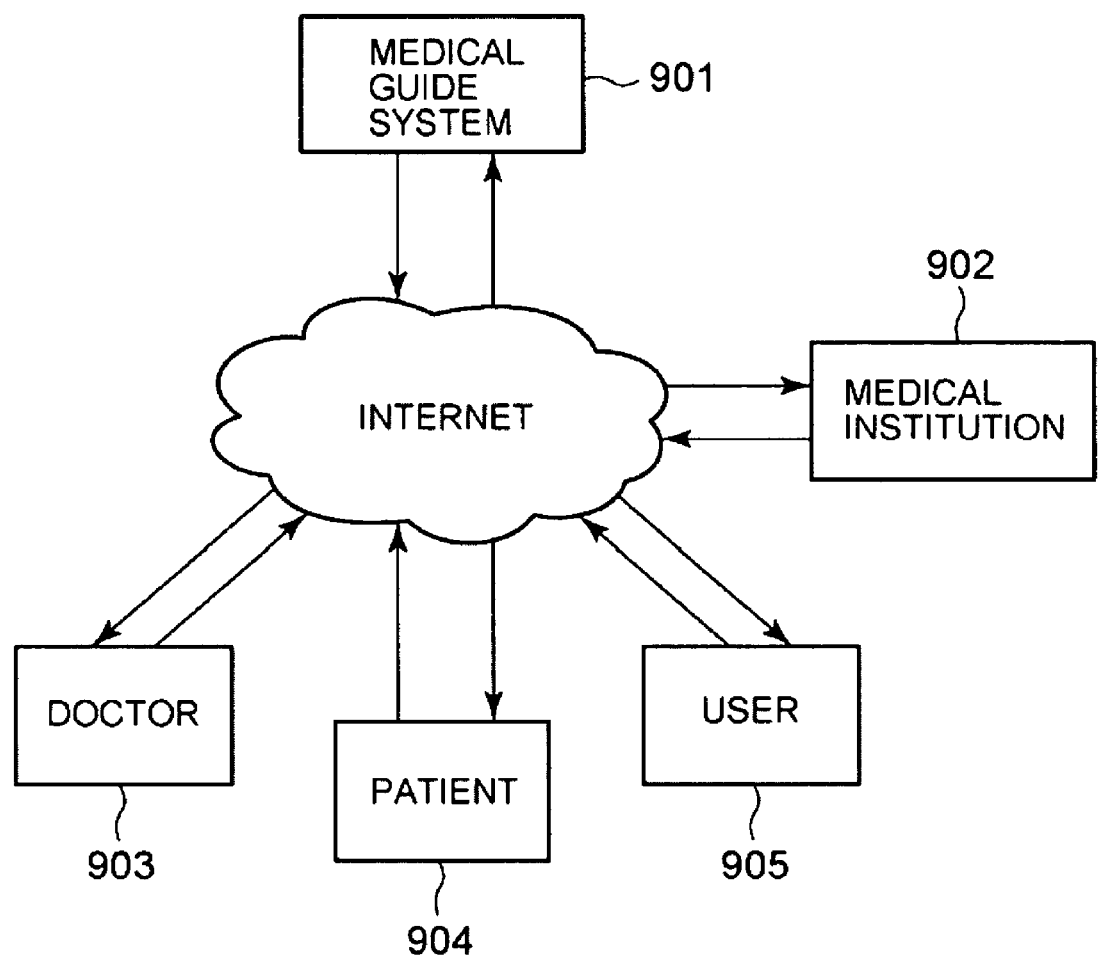

METHOD FOR CREATING MEDICAL TREATMENT MODELS FROM A DATABASE OF MEDICAL RECORDS

CROSS-REFERENCE TO RELATED APPLICATIONS

This application is filed under 35 U.S.C. 371(c) claiming priority of PCT Application No. PCT/JP2006/311533 filed Jun. 8, 2006 and Japanese Patent Application No. 2005-168921 filed Jun. 8, 2005, the entire text of which are specifically incorporated by reference herein.

TECHNICAL FIELD

The present invention relates to a technique for providing a medical guide service, and more particularly, to a technique for providing an appropriate medical guide service on the basis of the existing medical record data.

BACKGROUND ART

In general, a hospital has a large number of medical records. A doctor needs to examine a patient on the basis of his/her knowledge and experience and to determine appropriate examination and treatment. However, since the knowledge and experience of the doctor by himself or herself is limited, only the knowledge and experience of the doctor are insufficient to determine appropriate examination and treatment. Patent Document 1 discloses a technique for supporting the diagnosis by a doctor. Specifically, Patent Document 1 discloses a method of providing data matched with condition items that are input by a user and the ratio thereof, but does not disclose information indicating the kind of examination and treatment suitable for various conditions of a patient (at the time of the first medical examination, while being in a hospital, and after a surgical operation). In addition, Patent Document 1 does not consider the order of medical treatments including the chronological order of examination items and treatment behaviors.

[Patent Document 1]
JP-A-2004-185547 'System and Method for Analyzing Medical Data'

DISCLOSURE OF THE INVENTION

Problems to be Solved by the Invention

It is very important that a doctor determines appropriate examination items for a patient and then determines the kind of treatment behaviors suitable for the patient. The doctor determines the examination items and the treatment behaviors on the basis of the current examination result and diagnosis result, and previous experience. However, different medical treatments may be conducted on the same patient. In addition, there are various combinations of treatment behaviors to be selected. Therefore, a medical guide system enabling the doctor to reliably determine the kind of examination items and treatment behaviors suitable for a patient is needed. In addition, a medical guide system capable of providing appropriate examination item and treatment behavior on the basis of inexperienced examination results and diagnosis results is required.

The invention is designed to meet the needs, and an object of the invention to provide a medical guide system capable of determining appropriate examination item and treatment behavior on the basis of the examination results and the diagnosis results of a patent.

Another object of the invention is to provide a medical guide system enabling a doctor to reliably determine a treatment behavior suitable for a patient.

Still another object of the invention is to provide a medical guide system enabling a doctor to reliably determine examination items suitable for a patient.

Yet still another object of the invention is to provide a medical guide system capable of determining an examination and a medical treatment suitable for a patent on the basis of the examination results and the diagnosis results of the patient, and providing appropriate examination items and treatment behaviors including time-series elements.

Still yet another object of the invention is to provide a medical guide system that derives a rule from a large amount of medical record data in consideration of a plurality of examination items and treatment behaviors and displays the rule.

Yet still another object of the invention is to provide a medical guide system capable of providing appropriate medical guide services to a doctor, a patient, a general user, and a medical institution.

Means for Solving the Problems

According to a first aspect of the invention, a medical guide system includes: a unit that creates medical record data including examination data that includes examination items, the date and time of an examination, and examination results, and treatment data that includes treatment behaviors, the date and time of a medical treatment, and treatment results, the examination data and the treatment data being electronically recorded for every patient; a unit that extracts the medical record data for each patient, using the examination data before a predetermined dividing point in a chronological order as data before dividing point and the treatment data after the predetermined dividing point in the chronological order as data after dividing point; a unit that extracts a treatment pattern from a plurality of data after dividing point, the number of times that the treatment patter occurs is equal to or larger than a predetermined number of times; and a unit that derives a rule that associates the examination result with the treatment pattern from the treatment pattern and the data before dividing point data.

According to another aspect, preferably, the data after dividing point is the examination data and the treatment data after the predetermined dividing point, and the unit for extracting the treatment pattern extracts an examination pattern and a treatment pattern.

According to yet another aspect, preferably, when the treatment pattern is extracted, a treatment pattern having a chronological order including the order of treatments is also extracted.

According to still yet another aspect, preferably, machine learning is used to drive the rule.

According to yet still another aspect, preferably, when the rule is made, a rule having examination items and examination results as conditions and the treatment pattern as a conclusion is made from the treatment pattern and the data before dividing point.

According to still yet another aspect, preferably, the medical guide system further includes a unit that records the rule and searches a corresponding treatment pattern using the examination item and the examination result as search keys.

According to yet still another aspect, preferably, when the treatment pattern is extracted, a classification layer of the treatment behavior is used to extract the treatment pattern including the boarder concept of the treatment behavior emerged in the treatment data.

According to the invention, it is possible to provide medical guide services for appropriate examinations and treatments to a hospital and a medical facility, or doctors and nurses who are engaged in the hospital and the medical facility. In addition, a patient can remotely receive appropriate examination and treatment guide services through a network, such as the Internet, without going to the hospital. Further, a patient can access a website at the home to receive examination and treatment guide services. It is possible to create medical record data from medical records of a hospital having a high treatment performance and a high determining performance, and thus improve the reliability of a medical guide system according to the invention. For example, according to the invention, a hospital in a district without an advanced medical system can also receive a high-reliability medical guide service. That is, it is possible to reduce regional disparity in medical service. In addition, it is possible to prevent a medical accident and a medical mistake.

BRIEF DESCRIPTION OF THE DRAWINGS

FIG. 1 is a diagram illustrating one record of medical record data according to an embodiment of the invention.

FIG. 2 is a diagram illustrating an example of a classification system of examination items of examination data and a classification system of treatment behaviors of treatment data.

FIG. 4 is a diagram illustrating a pre-process for extracting a frequent generalized pattern.

FIG. 5 is a diagram illustrating a process of adding a set of frequent generalized patterns to a table A.

FIG. 6 is a diagram illustrating an example of the image of a rule obtained by a method according to an embodiment of the invention that is displayed on a GUI.

FIG. 7 is a diagram illustrating a list of patients satisfying conditions.

FIG. 8 is a flowchart illustrating a process of deriving a rule according to the embodiment of the invention.

FIG. 9 is a diagram illustrating a structure in which the system according to the invention is used as a medical guide system.

DESCRIPTION OF SYMBOLS

Figure 3:
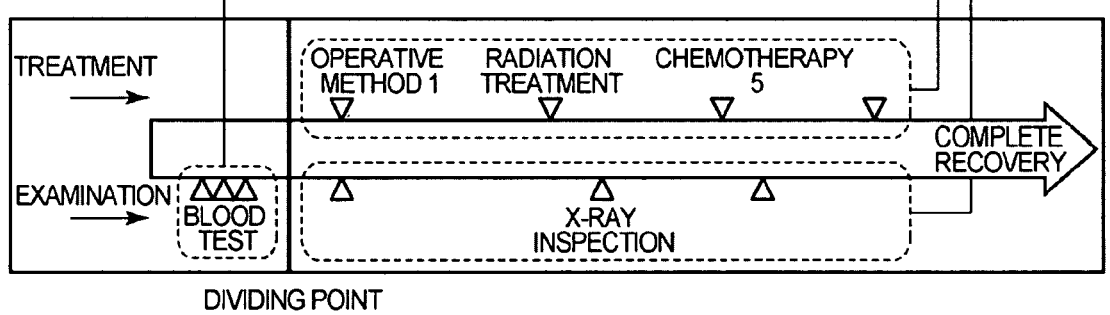
FIG. 3 is a diagram illustrating examination items and treatment behaviors of a patient arranged in the chronological order.

900: CPU
901: MEDICAL GUIDE SYSTEM
902: MEDICAL INSTITUTION
903: DOCTOR
904: PATIENT
905: USER
910: HOST CONTROLLER
920: CONTROLLER
930: ROM
935: KEYBOARD/MOUSE CONTROLLER
936: KEYBOARD
937: MOUSE
940: RAM
945: DRIVE
950: COMMUNICATION INTERFACE
960: SOUND CONTROLLER
965: SOUND INPUT/OUTPUT DEVICE
970: GRAPHIC CONTROLLER
975: DISPLAY DEVICE
980: HARD DISK DRIVE
985: FLEXIBLE DISK
990: MULTI COMBO DRIVE
995: DISK MEDIUM
990: MULTI COMBO DRIVE DRIVE
995: MEDIUM
1000: COMPUTER
1090: FLEXIBLE DISK
1095: CD-ROM

Best Mode for Carrying Out the Invention

Medical records are written on the paper or stored in the form of electronic data. The medical records include subjective information, such as patient's opinions, objective information, such as various doctors' medical opinions, assessment, and examination or treatment information. The medical record data used in this embodiment of the invention is electronic data of examination and treatment information on patients among the medical records. For example, hospitals use electronic medical records. In this case, since medical information on each patient is electronically recorded, a database storing the electronic medical records may be used without any change. The medical record data is composed of a plurality of records. One record corresponds to one patient, and includes examination data and treatment data. FIG. 1 shows one record of medical record data according to the invention. As shown in FIG. 1, a patient ID field, an examination data field, and a treatment data field are arranged from the left side. The examination data includes examination items, the date and time of an examination, and examination results. The examination results may include the information on date and time of the examination results. The treatment data includes information on a treatment behavior, the date and time of the treatment, and treatment results (outcome). The outcome information may include the date and time of the outcome. The medical record data may include information items other than the above-mentioned information items. A plurality of examination data components and a plurality of treatment data components may be provided. A plurality of examinations are conducted on a patient in an initial stage. Then, the patient is given a medical treatment according to the examination results. Since several examinations are conducted between treatment behaviors in order to obtain the effect of a treatment, a plurality of examination data and a plurality of treatment data generally exist. In addition, it goes without saying that the number of examination data and the number of treatment data depend on patients. In this embodiment, the examination data and the treatment data are stored in one record, but the invention is not limited thereto. When a patient ID is included, the examination data and the treatment data may be stored as independent records, which has no effect on the invention.

In this embodiment, the examination items mean detailed examination contents, such as a physical examination (a blood test and a urine examination), histodiagnosis, and cytologic diagnosis, and the treatment behaviors mean detailed behaviors, such as a surgical operation, a radiation treatment, chemotherapy, prescription, and a clinical trial. A classification system of the examination items of the examination data and a classification system of the treatment behaviors of the treatment data are shown in FIG. 2. For example, GOT, GPT, and γGTP are included in a liver function examination item in the classification system of the examination items, and total extirpation and partial excision are included in an ablative surgery item in the classification system of the treatment behaviors.

Paying attention to the patient recorded on the medical record data, the examination items and the treatment behaviors are arranged in the chronological order as shown in FIG. 3. This data is divided into two tables A and B before and after a predetermined dividing point. The table A is referred to as data before dividing point that includes data related to examination items and examination results before the dividing point in the chronological order. Table B is referred to as data after dividing point that includes data related to examination items and treatment behaviors after the dividing point in the chronological order. Preferably, the table B includes treatment results (outcome) and examination results. In particular, since information of outcome is very useful for a doctor, a patient, and a user, it is stored in an interesting place. This is because the information of outcome shows the pattern of treatment behaviors for allowing the patient to completely recover. The dividing point is a few days after the first medical examination, or a point of time when the value of the examination result is larger than a predetermined value. The dividing point may be determined by a person who receives a treatment behavior guide service. Since the position of the dividing point varies according to the patient, the date and time of the dividing point depend on the patient. The two tables are created for each record of medical record data, that is, for every patient.

FIG. 4 shows a pre-process for extracting a pattern. First, the table B is converted into transaction data. The transaction data is composed of an ID and items. In this embodiment, a transaction ID corresponds to a patient ID, and the items correspond to an examination item and a treatment item. A frequent generalized pattern is extracted from the transaction data. A frequent pattern will be described prior to the frequent generalized pattern. When the number of transactions including a set P of items as a subset is referred to a support degree, the frequent pattern means a pattern having a support degree that is larger than a threshold value designated by the user. All of the items in the pattern P are items of the transaction. When the item is matched with an upper-level item thereof, it is defined that the set P is a subset of a certain transaction. Therefore, the frequent generalized pattern is a frequent pattern based on the definition of the subset. When the table B is converted into transaction data in consideration of the chronological order of each row in the table B, it is possible to extract the frequent generalized pattern including the chronological order of examinations and medical treatments. In contrast, it is possible to extract the frequent generalized pattern without considering the chronological order of each row. In this case, when the frequent generalized pattern is extracted without considering the chronological order, but when a medical treatment behavior is guided, access to an individual pattern is performed, thereby performing a medical guide including the chronological order. A minimum support degree (threshold value) is set, and all of the frequent generalized patterns are extracted from the transaction data, thereby creating a table C.

The following process is performed on elements in a set (table C) of the extracted frequent generalized patterns. A flag is given to a 'patient subjected to a combination of medical treatment behaviors', paying attention to one frequent generalized pattern (a combination of medical treatment behaviors) of the table C. Specifically, information T on the 'patient subjected to a combination of medical treatment behaviors' is added to the rightmost side of a table that is formed by integrating the tables A corresponding to the number of patients. In contrast, information F on a 'patient not subjected to a combination of medical treatment behaviors' is added to create a table D (FIG. 5). Machine learning using, for example, inductive logic programming, is applied to the table D to create a rule related to a combination of interesting medical treatment behaviors. The machine learning is a method of extracting from data a general rule for describing characteristics of the data. Various machine learning methods have been known. It is preferable that the learning be performed by a teacher. Since the machine learning is beyond the scope of the invention, a detailed description thereof will be omitted. Any existing method may be used as the machine learning method. In the case of a method that cannot deal with a numerical attribute, discretization is performed beforehand. The machine learning is applied to a plurality of created tables D to derive a rule having a specific examination item and an examination result as conditions and a treatment behavior pattern as a conclusion. The rule serves as a medical guide. The medical guide can be sufficiently used without any change. However, preferably, the derived rule is recorded as a table to add a search function, which makes it possible for the user to input an examination item and an examination result as search keys, thereby searching a corresponding treatment behavior pattern.

FIG. 6 shows an example of the image of the rule obtained by the method according to the embodiment, which is displayed on a GUI. For example, in FIG. 6, a first row indicates that a patient satisfying the conditions of the examination result of an examination item has a surgical operation with an operation code 087654321 and the number of patients is 18. In addition, as can be seen from FIG. 6, overcome (complete recovery, remission, ingravescence, and death) is added to the table B, and information of outcome is also shown in FIG. 6. In FIG. 6, for easy viewing, the information of outcome is written in an independent row. In addition, an examination pattern as well as the medical treatment behavior pattern can be extracted as a rule. Examination data after the dividing point is also used to create the table B. The kind of examination to be performed after a medical treatment is conducted can be represented by a rule. In FIG. 6, it is noted that a bad medical treatment pattern as well as a good medical treatment pattern may be derived as a rule. This rule is also an important factor.

When the user clicks the first row of FIG. 6 using a mouse, a list of 19 patients satisfying the conditions is displayed as shown in FIG. 7. FIG. 7 shows attributes related to the patients, such as 18 patient IDs and their names. In addition, when the user clicks a specific patient among 18 patients using the mouse, electronic medical record information of the patient is displayed, and thus the user can know detailed examination and treatment courses. Since a read function shown in FIG. 7 is used to access private information of the patient, only a person having an access authority is allowed to use the read function.

FIG. 8 is a flowchart illustrating a process of creating a rule according to the invention. First, in Step 810, electronic medical record data is created. Examination data and treatment data for each patient are extracted from the medical record. In Step 820, the table A is created before a predetermined dividing point in the chronological direction of the medical record data, and the table B is created after the predetermined dividing point in the chronological direction. The predetermined dividing point can be designated by the user who operates the medical guide system according to this embodiment. The table A includes examination data, and the table B preferably includes the examination data and the treatment data. Alternatively, the table B may include only the treatment data. In this case, the effect of the invention can also be obtained. In Step 830, the table B is converted into transaction data. The patient ID is allocated to a transaction data ID, and the examination data and the treatment data are allocated to items. In Step 840, the table C, which is the frequent generalized pattern, is created from the transaction data. The frequent generalized pattern is a pattern that is classified in consideration of a subset in the examination pattern and the treatment pattern applied to the patient. In addition, the frequent generalized pattern is a pattern whose frequency is larger than a predetermined number of frequencies. The table C is added to a table obtained by integrating the tables A corresponding to the number of patients, thereby creating the table D. That is, the table D makes it possible to know whether the frequent generalized pattern is applied to each patient. Finally, in Step 860, the existing machine learning method is used to extract a rule from the frequent generalized pattern. That is, the rule has content capable of guiding the kind of examination and treatment to be considered from specific examination data. When medical record data, which is a source, is created from a large number of medical records of a good medical institution, it is possible to provide a medical guide service having high reliability.

FIG. 9 is a diagram illustrating a medical guide system to which the system according to the invention is applied. A medical guide system 901 includes the main components of the invention. A medical institution 902 is a medical facility, such as a hospital, a medical office, or a public health center. A doctor 903 is a person who is engaged in the medical practice. A patient 904 is a person who receives a medical guide service. A user 905 is a person who uses the medical guide service. The medical guide system 901, the medical institution 902, the doctor 903, the patient 904, and the user 905 are connected to one another through a network (typically, Internet).

As a typical configuration, the medical institution 902 is provided with the medical guide system 901, and the doctor 903 working in the medical institution 902 treats the patient 904 who is registered or entered in the medical institution 902. In this case, it is considered that the patient 904 accesses the medical guide system 901 to receive a medical guide service. In general, the doctor 903 gives an advice or a medical guide to the patient 902 in the medical institution 902. However, it does not matter when the doctor 903 is spaced from the patient 904. The medical guide system 901 may not be installed in the medical institution 902. In addition, the doctor 903 may remotely provide a medical guide service to the patient in a place out of the hospital, for example, at the home.

As another configuration, the medical institution 902 may directly access the medical guide system 901, and read out all data from the medical guide system 901 to create a printed matter, such as a medical guidebook, or an electronic medium. When a plurality of medical guide systems 901 are installed, it is possible to integrate a plurality of medical guides. For example, when the medical guide system 902 cannot access a network, it is possible to locally refer to a printed matter, such as a medical guidebook, or an electronic medium that is created beforehand, thereby providing a medical guide service. The medical guidebook may be sent to another medical institution that is not connected to the network by mail.

As still another configuration, when the doctor 903 is absent, the patient 904 can access the medical guide system 901 to check which kind of examination and treatment will be performed on the basis of his or her examination data. In this case, preferably, the medical institution 902 is interposed between the patient 904 and the medical guide system 901, and the patient 904 logs in the medical guide system 901 through the medical institution 902.

As yet another configuration, the user 905 at the home accesses the medical guide system 901 to receive a medical guide service. For example, the user may acquire his or her previous examination data from the medical institution 902 and use the acquired data to know what kind of treatment has been performed, or the user may receive an examination or treatment guide service that will be considered from the examination data of a family or acquaintances.

As still yet another configuration, a company equipped with the medical guide system 901 may access the medical guide system 901 to charge and collect a medical service fee from the doctor 903, the medical institution 902, and the user 905 according to the number of accesses to the medical guide system 901. In addition, various modifications and changes of the invention can be made without departing from the scope and spirit of the invention.

Figure 10:
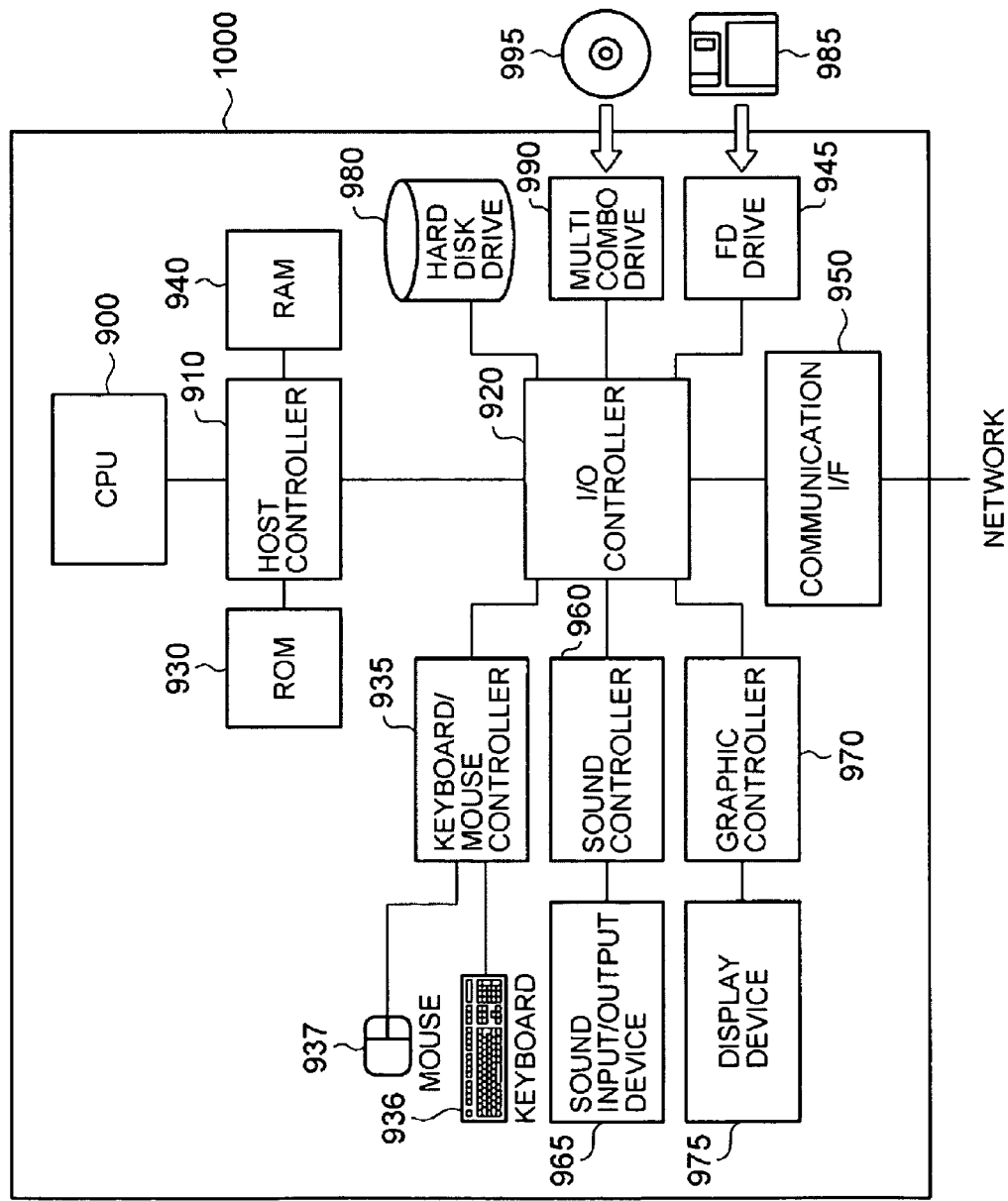
FIG. 10 is a diagram illustrating an example of the hardware structure of a medical guide system according to the invention.

FIG. 10 is a diagram illustrating the hardware structure of the medical guide system according to the embodiment of the invention. A computer 1000, serving as the medical guide system, includes: a CPU peripheral section having a CPU 900, a RAM 940, a ROM 930, and an I/O controller 920 that are connected to one another by a host controller 910; a communication interface 950 connected to the I/O controller 920; a hard disk drive 980; a multi combo driver 990 that can read/write data from/on a disk medium 995, such as a CD or a DVD; a FD drive 945 that can read/write data from/on a flexible disk 985; a sound controller 960 that drives a sound input/output device 965; a graphic controller 970 that drives a display device 975; and a keyboard/mouse controller 935 that controls a keyboard 936 and a mouse 937.

The CPU 900 operates on the basis of programs stored in the ROM 930, a BIOS, and the RAM 940 to control these components. The graphic controller 970 acquires image data buffered by a frame buffer that is provided in the RAM 940 of the CPU 900, and displays the image data on the display device 975. Alternatively, the graphic controller 970 may be provided with a frame buffer that stores image data generated by, for example, the CPU 900. Preferably, the output of the medical guide•system according to the invention is displayed on a GUI of the display device 975. The user uses the mouse 937 to display a desired medical guide corresponding to the displayed examination item, and if necessary, the user uses the keyboard 936 to input data.

The communication interface 950 communicates with the medical institution 902, another medical guide system 901, the doctor 903, the patient 904, and the user 905 over a network. In addition, the network may be formed by short distance communication, such as wire communication, wireless communication, infrared communication, or BLUETOOTH. In this case, the configuration of the invention can also be used without any change. The hard disk drive 980 stores codes of programs that allow the computer 1000 to execute operations based on the flowchart shown in FIG. 8, electronic medical record•data, and an OS. The multi combo drive 990 reads out electronic medical record data and programs from the medium 995, such as a CD or a DVD. The programs and data read from these storage units are loaded to the RAM 940 such that the CPU 900 can use the programs and data. The electronic medical record data or the programs required for the invention may be supplied from an external storage medium. Alternatively, they may be supplied from an internal hard disk drive 980 or downloaded through a network.

The storage media include a flexible disk 1090, a CD-ROM 1095, an optical recording medium, such as a DVD or a PD, a magneto-optical recording medium, such as an MD, a tape medium, and a semiconductor memory, such as an IC card. In addition, a storage device, such as a RAM or a hard disk that is provided in a server system connected to a dedicated communication network or the Internet, may be used as a recording medium, and programs and data may be downloaded from the recoding medium over the network. It will be understood by those skilled in the art that the hardware structure is just an illustrative example, and all of the components are not indispensable components. As can be known from the above-mentioned structure, any kind of hardware structure can be used as the hardware structure according to the invention, as long as it has the function of a general computer. For example, a mobile terminal, a portable digital assistant, a computer appliance, and a dedicated hardware structure having a CPU, a memory, a display device, and a communication function may be used as the hardware structure of the invention.

Although the embodiment of the invention has been described above, the invention is not limited thereto. Various modifications and changes of the invention can be made without departing from the spirit and technical scope of the invention. The technical scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A medical guide system comprising:
    a unit that creates medical record data including examination data that includes examination items, the date and time of an examination, and examination results, and treatment data that includes treatment behaviors, the date and time of a medical treatment, and treatment results, the examination data and the treatment data being electronically recorded for every patient;
    a unit that extracts the medical record data for each patient, and uses the examination data before a predetermined dividing point in a chronological order as before-dividing-point data and the treatment data after the predetermined dividing point in the chronological order as after-dividing-point data;
    a unit that extracts a treatment pattern from the after-dividing-point data, wherein the frequency that the treatment pattern occurs is equal to or greater than a predetermined number; and
    a unit that derives a rule, using at least one computer processor, that associates the examination results with the treatment pattern from the treatment pattern and the before-dividing-point data.

2. The medical guide system according to claim 1, wherein the after-dividing-point data is the examination data and the treatment data after the predetermined dividing point, and the unit that extracts the treatment pattern extracts an examination pattern and the treatment pattern.

3. The medical guide system according to claim 1, wherein the unit that extracts the treatment pattern extracts the treatment pattern having a chronological order including an order of treatments.

4. The medical guide system according to claim 1, wherein the unit that derives the rule uses machine learning to derive the rule.

5. The medical guide system according to claim 1, wherein the unit that derives the rule derives the rule having examination items and examination results as conditions and the treatment pattern as a conclusion, from the treatment pattern and the before-dividing-point data.

6. The medical guide system according to claim 1, wherein the predetermined dividing point is designated by a user.

7. The medical guide system according to claim 1, wherein the predetermined number is a threshold value that is designated by a user.

8. The medical guide system according to claim 1, further comprising:
    a unit that records the derived rule and searches a corresponding treatment pattern using the examination items and the examination results as search keys.

9. The medical guide system according to claim 1, wherein the unit that extracts the treatment pattern uses a classification layer of the treatment behaviors to extract the treatment pattern and the treatment behaviors emerged in the treatment data.

10. The medical guide system according to claim 1, wherein the examination items include a physical examination, histodiagnosis, and cytologic diagnosis, and the treatment behaviors include a surgical operation, a radiation treatment, chemotherapy, a prescription, and a clinical trial.

11. The medical guide system according to claim 1, wherein the system is connected to a network, and the system further includes:
    a unit that receives a specific examination result from a computer connected to the network; and
    a unit that searches a treatment pattern corresponding to the specific examination result from the rule of the system, and transmits the treatment pattern to the computer.

12. The medical guide system according to claim 11, wherein the specific examination result is an examination result of a patient or a general user connected to the network.

13. The medical guide system according to claim 11, wherein the computer is part of a medical institution that is connected to the network, and the specific examination result is an examination result of a patient who is registered in the medical institution.

14. The medical guide system according to claim 11, wherein the computer is a computer of a doctor connected to the network, and the specific examination result is an examination result of a patient who is treated by the doctor.

15. A medical guide method comprising the steps of:
    creating medical record data including examination data that includes examination items, the date and time of an examination, and examination results, and treatment data that includes treatment behaviors, the date and time of a medical treatment, and treatment results, the examination data and the treatment data being electronically recorded for every patient;
    extracting the medical record data for each patient, using the examination data before a predetermined dividing point in a chronological order as before-dividing-point data and the treatment data after the predetermined dividing point in the chronological order as after-dividing-point data;
    extracting a treatment pattern from the after-dividing-point data, wherein the frequency that the treatment pattern occurs is equal to or greater than a predetermined number; and deriving a rule, using at least one computer processor, that associates the examination results with the treatment pattern from the treatment pattern and the before-dividing-point data.

16. A non-transitory computer readable medium comprising a medical guide program for allowing a computer to execute the steps of:

creating medical record data including examination data that includes examination items, the date and time of an examination, and examination results, and treatment data that includes treatment behaviors, the date and time of a medical treatment, and treatment results, the examination data and the treatment data being electronically recorded for every patient;

extracting the medical record data for each patient, using the examination data before a predetermined dividing point in a chronological order as before-dividing-point data and the treatment data after the predetermined dividing point in the chronological order as after-dividing-point data;

extracting a treatment pattern from the after-dividing-point data, wherein the frequency that the treatment pattern occurs is equal to or greater than a predetermined number; and deriving a rule that associates the examination results with the treatment pattern from the treatment pattern and the before-dividing-point data.

* * * * *